(12) United States Patent
Havre et al.

(10) Patent No.: US 6,210,916 B1
(45) Date of Patent: Apr. 3, 2001

(54) REC 2 KINASE

(75) Inventors: Pamela A. Havre, Philadelphia; Michael C. Rice, Newtown, both of PA (US); William K. Holloman, Yorktown Heights, NY (US); Eric B. Kmiec, Yardley, PA (US)

(73) Assignees: Thomas Jefferson University, Philadelphia, PA (US); Cornell Research Foundation Inc., Ithaca, NY (US); Valigen (US), Inc., Newtown, PA (US)

( * ) Notice: Subject to any disclaimer, the term of this patent is extended or adjusted under 35 U.S.C. 154(b) by 0 days.

(21) Appl. No.: 09/587,436

(22) Filed: Jun. 5, 2000

Related U.S. Application Data

(62) Division of application No. 09/157,603, filed on Sep. 21, 1998.

(51) Int. Cl.[7] .............................. C12Q 1/48; C12N 9/12; C07K 1/00
(52) U.S. Cl. ............................ 435/15; 435/194; 530/350
(58) Field of Search ........................ 424/194.5; 435/194, 435/15; 530/350

(56) References Cited

PUBLICATIONS

Struzbecher et al., EMBO J., 15(8), 1992–2002 (Apr. 1996).
Bjorbaek et al., "Identification of a Novel Human RAD 51 Homolog, RAD51B", Genomics, vol. 46, p. 476–479, 1997.
Albala, J.S., et al., "Identification of a Novel Human *RAD 51*" Homolog, *RAD51B,* Genomics, Vol. 46, pp. 476–479, 1997.
Agarwal, M.L., et al., "the p53 Network", The Journal of Biological Chemistry, vol. 273, No. 1. p. 1–4, Jan. 2, 1998.
Cartwright R., et al., "Isolation of novel human and mouse genes of the recA/RAD51 recombination–repair gene family", Nucleic Acids Research, vol. 26, No. 7, p. 1653–1659, 1998.
Rice, M.C., et al., "Isolation of human and mouse genes based on homology to REC2, a recombinational repair gene from the fungus *Ustilago maydis*" Proceedings of the National Academy of the Sciences, vol. 94, p. 7417–7422, Jul. 1997.

*Primary Examiner*—Rebecca E. Prouty
*Assistant Examiner*—M. Monshipouri
(74) *Attorney, Agent, or Firm*—Seidel, Gonda, Lavorgna & Monaco, PC

(57) ABSTRACT

The invention includes a method of phosphorylating a serine containing substrate by incubating the substrate with ATP and an enzyme that is hsRec2 or muRec2 or a derivative thereof. The natural substrates of the kinase activity of Rec2 are the cell cycle control proteins such as p53 and cyclin E. The over expression of Rec2 is known to cause cell-cycle arrest and apoptosis and the invention discloses that these effects are kinase mediated. Accordingly, the invention provides a method of assessing antagonists and agonists of Rec2, which antagonists and agonists would have pharmacological activity. The invention further discloses that there is specific binding between hsRec2 and at least three cell cycle control proteins: p53, PCNA and cdc2.

14 Claims, 13 Drawing Sheets

Figure 2B:
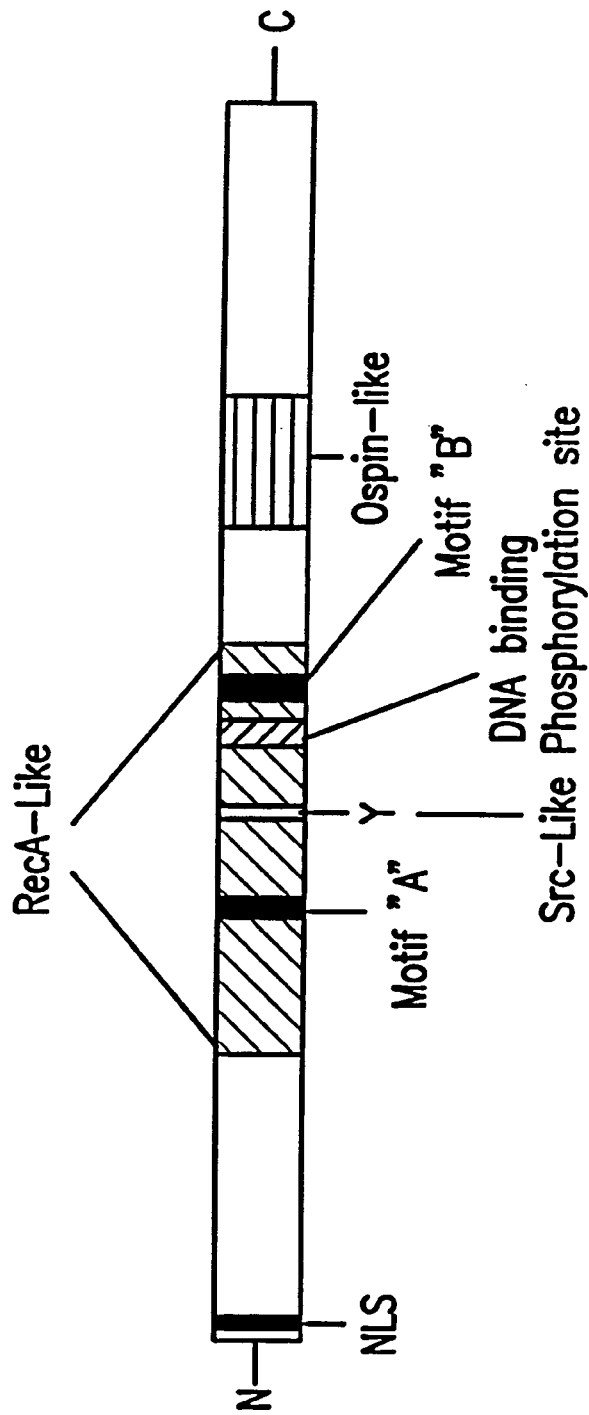

Met Gly Ser Lys Lys Leu Lys Arg Val Gly Leu Ser Gln Glu Leu Cys
 1                   5                  10                  15
Asp Arg Leu Ser Arg His Gln Ile Leu Thr Cys Gln Asp Phe Leu Cys
                    20                  25                  30
Leu Ser Pro Leu Glu Leu Met Lys Val Thr Gly Leu Ser Tyr Arg Gly
                35                  40                  45
Val His Glu Leu Leu Cys Met Val Ser Arg Ala Cys Ala Pro Lys Met
            50                  55                  60
Gln Thr Ala Tyr Gly Ile Lys Ala Gln Arg Ser Ala Asp Phe Ser Pro
 65                  70                  75                  80
Ala Phe Leu Ser Thr Thr Leu Ser Ala Leu Asp Glu Ala Leu His Gly
                    85                  90                  95
Gly Val Ala Cys Gly Ser Leu Thr Glu Ile Thr Gly Pro Pro Gly Cys
                100                 105                 110
Gly Lys Thr Gln Phe Cys Ile Met Ser Ile Leu Ala Thr Leu Pro
                115                 120                 125
Thr Asn Met Gly Gly Leu Glu Gly Ala Val Val Tyr Ile Asp Thr Glu
 130                 135                 140
Ser Ala Phe Ser Ala Glu Arg Leu Val Glu Ile Ala Glu Ser Arg Phe
 145                 150                 155                 160
Pro Arg Tyr Phe Asn Thr Glu Glu Lys Leu Leu Leu Thr Ser Ser Lys
                165                 170                 175

FIG.1A

Val His Leu Tyr Arg Glu Leu Thr Cys Asp Glu Val Leu Gln Arg Ile
                180                 185                 190

Glu Ser Leu Glu Glu Ile Ile Ser Lys Gly Ile Lys Leu Val Ile
            195                 200                 205

Leu Asp Ser Val Ala Ser Val Arg Lys Glu Phe Asp Ala Gln Leu
210                 215                 220

Gln Gly Asn Leu Lys Glu Arg Asn Lys Phe Leu Ala Arg Glu Ala Ser
225                 230                 235                 240

Ser Leu Lys Tyr Leu Ala Glu Phe Ser Ile Pro Val Ile Leu Thr
            245                 250                 255

Asn Gln Ile Thr His Leu Ser Gly Ala Leu Ala Ser Gln Ala Asp
        260                 265                 270

Leu Val Ser Pro Ala Asp Asp Leu Ser Leu Ser Glu Gly Thr Ser Gly
275                 280                 285

Ser Ser Cys Val Ile Ala Ala Leu Gly Asn Thr Trp Ser His Ser Val
290                 295                 300

Asn Thr Arg Leu Ile Leu Gln Tyr Leu Asp Ser Glu Arg Arg Gln Ile
305                 310                 315                 320

Leu Ile Ala Lys Ser Pro Leu Ala Pro Phe Thr Ser Phe Val Tyr Thr
            325                 330                 335

Ile Lys Glu Gly Leu Val Leu Gln Ala Tyr Gly Asn Ser
340                 345                 350

FIG.1B

| | | | | 60 |
|---|---|---|---|---|
| CGGACGCCGTG | GGCGCGGGGA | AACTGTGTAA | AGGGTGGGGA | AACTTGAAAG | TTGGATGCTG |
| CAGACCCGGC | ATGGGTAGCA | AGAAACTAAA | ACGAGTGGGT | TTATCACAAG | AGCTGTGTGA | 120
| CCGTCTGAGT | AGACATCAGA | TCCTTACCTG | TCAGGACTTT | TTATGTCTTT | CCCCACTGGA | 180
| GCTTATGAAG | GTGACTGGTC | TGAGTTATCG | AGGTGTCCAT | GAACTTCTAT | GTATGGTCAG | 240
| CAGGGCCTGT | GCCCCAAAGA | TGCAAACGGC | TTATGGGATA | AAAGCACAAA | GGTCTGCTGA | 300
| TTTCTCACCA | GCATTCTTAT | CTACTACCCT | TTCTGCTTTG | GACGAAGCCC | TGCATGGTGG | 360
| TGTGGCTTGT | GGATCCCTCA | CAGAGATTAC | AGTTCCACCA | GGTTGTGGAA | AAACTCAGTT | 420
| TTGTATAATG | ATGAGCATTT | TGGCTACATT | ACCCACCAAC | ATGGGAGGAT | TAGAAGGAGC | 480
| TGTGGTGTAC | ATTGACACAG | AGTCTGCATT | TAGTGCTGAA | AGACTGGTTG | AAATAGCAGA | 540
| ATCCCGTTT | CCCAGATATT | TTAACACTGA | AGAAAAGTTA | CTTTTGACAA | GTAGTAAAGT | 600
| TCATCTTTAT | CGGGAACTCA | CCTGTGATGA | AGTTCTACAA | AGGATTGAAT | CTTTGGAAGA | 660
| AGAAATTATC | TCAAAAGGAA | TTAAACTTGT | TCTCAAAGAA | TCTGTTGCTT | CTGTGGTCAG | 720
| AAAGGAGTTT | GATGCACAAC | TTCAAGGCAA | TCTCAAAGAA | AGAAACAAGT | TCTTGGCAAG | 780
| AGAGGCATCC | TCCTTGAAGT | ATTGGCTGA | GGAGTTTTCA | ATCCCAGTTA | TCTTGACGAA | 840
| TCAGATTACA | ACCCATCTGA | GTGGAGCCCT | GCTTCTCCAG | GCAGACCTGG | TGTCTCCAGC | 900

FIG.1C

```
TGATGATTTG TCCCTGTCTG AAGGCACTTC TGGATCCAGC TGTGTGATAG CCGCACTAGG    960
AAATACCTGG AGTCACAGTG TGAATACCCG GCTGATCCTC CAGTACCTTG ATTCAGAGAG   1020
AAGACAGATT CTTATTGCCA AGTCCCCTCT GGCTCCCCTC ACCTCATTTG TCTACACCAT   1080
CAAGGAGGAA GGCCTGGTTC TTCAAGCCTA TGGAAATTCC TAGAGACAGA TAAATGTGCA   1140
AACCTGTTCA TCTTGCCAAG AAAAATCCGC TTTTCTGCCA CAGAAACAAA ATATTGGGAA   1200
AGAGTCTTGT GGTGAAACAC CCATCGTTCT CTGCTAAAAC ATTTGGTTGC TACTGTGTAG   1260
ACTCAGCTTA AGTCATGGAA TTCTAGAGGA TGTATCTCAC AAGTAGGATC AAGAACAAGC   1320
CCAACAGTAA TCTGCATCAT AAGCTGATTT GATACCATGG CACTGACAAT GGGCACTGAT   1380
TTGATACCAT GGCACTGACA ATGGGAACAG AGGGAACAGG AAATGGGAAT GAGAGCAAGG   1440
GTTGGGTTGT GTTCGTGGAA CACATAGGTT TTTTTTTTTA ACTTTCTCTT TCTAAAATAT   1500
TTCATTTTGA TGGAGGTGAA ATTTATATAA GATGAAATTA ACCATTTTAA AGTAAACAAT   1560
TCCGTGGCAA CTAGATATCA TGATGTGCAA CCAGCATCTC TGTCTAGTTC CCAAATATTT   1620
CATCACCCCC AAAAGCAAGA CCCATAACCA TTATGCAAGT GTTCCTATTT CCCCCTCCTC   1680
CCAGCTCCTG GGAAACCACC AATCTACTTT TTTTCTATGG CTTTACCTAA TCTGGAAATT   1740
TCAAATAAAT GGGATCAAAT AGTTTCCCAA AAAAAAAAAA AAAAAAA                1797
```

FIG.1D

```
Met Ser Ser Lys Lys Leu Arg Arg Val Gly Leu Ser Pro Glu Leu
 1                       5                      10                      15
Asp Arg Leu Ser Arg Tyr Leu Ile Val Asn Cys Gln His Phe Leu Ser
                        20                      25                      30
Leu Ser Pro Leu Glu Leu Met Lys Val Thr Gly Leu Ser Tyr Arg Gly
                        35                      40                      45
Val His Glu Leu Leu His Thr Val Ser Lys Ala Cys Ala Pro Gln Met
 50                      55                      60
Gln Thr Ala Tyr Glu Leu Lys Thr Arg Arg Ser Ala His Leu Ser Pro
 65                      70                      75                      80
Ala Phe Leu Ser Thr Thr Leu Cys Ala Leu Asp Glu Ala Leu His Gly
                        85                      90                      95
Gly Val Pro Cys Gly Ser Leu Thr Glu Ile Thr Gly Pro Pro Gly Cys
                       100                     105                     110
Gly Lys Thr Gln Phe Cys Ile Met Met Ser Val Leu Ala Thr Leu Pro
                       115                     120                     125
Thr Ser Leu Gly Gly Leu Glu Gly Ala Val Val Tyr Ile Asp Thr Glu
                       130                     135                     140
Ser Ala Phe Thr Ala Glu Arg Leu Val Glu Ile Ala Glu Ser Arg Phe
 145                     150                     155                     160
Pro Gln Tyr Phe Asn Thr Glu Glu Lys Leu Leu Leu Thr Ser Ser Arg
                       165                     170                     175
```

FIG.1E

FIG.1F

```
Val His Leu Cys Arg Glu Leu Thr Cys Glu Gly Leu Leu Gln Arg Leu
            180             185             190
Glu Ser Leu Glu Glu Ile Ile Ser Lys Gly Val Lys Leu Val Ile
    195             200             205
Val Asp Ser Ile Ala Ser Val Arg Lys Glu Phe Asp Pro Lys Leu
    210             215             220
Gln Gly Asn Ile Lys Glu Arg Asn Lys Phe Leu Gly Lys Gly Ala Ser
225             230             235             240
Leu Leu Lys Tyr Leu Ala Gly Glu Phe Ser Ile Pro Val Ile Leu Thr
            245             250             255
Asn Gln Ile Thr His Leu Ser Gly Ala Leu Pro Ser Gln Ala Asp
            260             265             270
Leu Val Ser Pro Ala Asp Asp Leu Ser Leu Ser Glu Gly Thr Ser Gly
    275             280             285
Ser Ser Cys Leu Val Ala Ala Leu Gly Asn Thr Trp Gly His Cys Val
290             295             300
Asn Thr Arg Leu Ile Leu Gln Tyr Leu Asp Ser Glu Arg Arg Gln Ile
305             310             315             320
Leu Ile Ala Lys Ser Pro Leu Ala Ala Phe Thr Ser Phe Val Tyr Thr
            325             330             335
Ile Lys Gly Glu Gly Leu Val Leu Gln Gly His Gly His Glu Arg Pro
340             345             350
```

| | | | | |
|---|---|---|---|---|
| GGGAGCCCTG | GAAACATGAG | CAGCAAGAAA | CTAAGACGAG | TGGGTTTATC | TCCAGAGCTG | 60 |
| TGTGACCGTT | TAAGCAGATA | CCTGATTGTT | AACTGTCAGC | ACTTTTTAAG | TCTCTCCCCA | 120 |
| CTAGAACTTA | TGAAAGTGAC | TGGCCTGAGT | TACAGAGGTG | TCCACGAGCT | TCTTCATACA | 180 |
| GTAAGCAAGG | CCTGTGCCCC | GCAGATGCAA | ACGGCTTATG | AGTTAAAGAC | ACGAAGGTCT | 240 |
| GCACATCTCT | CACCGGCATT | CCTGTCTACT | ACCCTGTGCG | CCTGGATGA | AGCATTGCAC | 300 |
| GGTGGTGTGC | CTTGTGGATC | TCTCACAGAG | ATTACAGTC | CACCAGTTG | CGGAAAAACT | 360 |
| CAGTTTTGCA | TAATGATGAG | TGTCTTAGCT | ACATTACCTA | CCAGCCTGGG | AGGATTAGAA | 420 |
| GGGGCTGTGG | TCTACATCGA | CACAGAGTCT | GCATTTACTG | CTGAGAGACT | GGTTGAGATT | 480 |
| GCGGAATCTC | GTTTCCACA | ATATTTTAAC | ACTGAGGAAA | AATTGCTTCT | GACCAGCAGT | 540 |
| AGAGTTCATC | TTTGCCGAGA | GCTCACCTGT | GAGGGCTTC | TACAAAGGCT | TGAGTCTTTG | 600 |
| GAGGAAGAGA | TCATTTCGAA | AGGAGTTAAG | CTTGTGATTG | TTGACTCCAT | TGCTTCTGTG | 660 |
| GTCAGAAAGG | AGTTTGACCC | GAAGCTTCAA | GGCAACATCA | AAGAAAGGAA | CAAGTTCTTG | 720 |
| GGCAAAAGGA | CGTCCCTTACT | GAAGTACCTG | GCAGGGGAGT | TTTCAATCCC | AGTTATCTTG | 780 |
| ACGAATCAAA | TTACGACCCA | TCTGAGTGGA | GCCCTCCCTT | CTCAAGCAGA | CCTGGTGTCT | 840 |
| CCAGCTGATG | ATTTGTCCCT | GTCTGAAGGC | ACTTCTGGAT | CCAGTCTGTTT | GGTAGCTGCA | 900 |
| CTAGGAAACA | CATGGGGTCA | CTGTGTGAAC | ACCCGGCTGA | TTCTCCAGTA | CCTGATTCA | 960 |
| GAGAGAAGGC | AGATTCTCAT | TGCCAAGTCT | CCTCTCGGCTG | CCTTCACCTC | CTTTGTCTAC | 1020 |
| ACCATCAAGG | GGGAAGGCCT | GGTTCTTCAA | GGCCACGAAA | GACCATAGGG | ATACTGTGAC | 1080 |
| CTTTGTCTAG | TGCTGATTGC | ATGTGACTCA | TGAAATGAAA | CAGGACTGCG | CTGCTTGGAA | 1140 |
| AAAGGAAACG | GAAGCCAACA | GGTTCTTCAA | TAATTGGTTG | GTTGCTGTTG | CAGGTGGTAAC | 1200 |
| AGTGATTTCA | GACCCCGAAG | GAAGCCTTT | AGAAGCCTTC | ATCCAGTCTC | TGGATGCAGA | 1260 |
| GGCTAGGGGC | TCCACCACCG | TGGGATGTCA | GCGGCCATCG | TAATAATTTG | CACTTACACA | 1320 |
| AGCACCTTTC | AGCCATGCCC | CTCAAAGTGT | TTCAGCCACA | TTAATTAATT | AAAGCCACCA | 1380 |
| ATCCCCCTAG | GGAGAGCAGG | AGGGGACTA | ACAAGATTTG | TAATTACAGA | AGGGAAAATT | 1440 |
| TCCGAATAAA | GTATTGTTCC | GCCAAAAAAA | AAAAAAAAAA | AAAAAAAAAA | AAAAAAAAAA | 1500 |
| AAAAAAAAAA | AAAAA | | | | | 1525 |

FIG.1G

MGSKKLKRVGLSQELCDRLSRHQILTCQDFLCLSPLELMKVTGLS
    NLS
YRGVHELLCMVSRACAPKMQTAYGIKAQRSADFSPAFLSTILSA
                                          50
LDEALHGGVACGSLTEITGPPGCGKTQFCIMMSILATLPTNMGGL
                      100   A BOX
EGAVVYIDTESAFSAERLVEIAESREPRYFNTEEKLLLTSSKVHLY
                  150                  P
RELTCDEVLQRIESLEEEIISKGIKLVILDSVASVVRKEFDAQLQG
  DNA            200     B BOX
NLKERNKFLAREASSLKYLAEEFSIPVILTNQITHLSGALASQAD
                              250
LVSPADDLSLSEGTSGSSSCVIAALGNTWSHSVNTRLILQYLDSERR
                          300
QILIAKSPLAPFTSFVYTIKEEGLVLQAYGNS*
                350

FIG.2A

```
U.m.   124  LNDARFASSCIVPPTQGYDGNFPGAQCFVYDSDAGSDSDARSSIDAVMHE  173
            ::   ::       .|.::  .|:|::    .:::
Human    1  MGSKKLKR...VGLSQELCDRLSRHQILTCQDFLCLSPLELMKVTGLSYR   47

174  DI.ELPSTFCRPQTPQTHDVARDEHHDGYLCDPKVDHASVARDVLSLGRQ  222
            ::  |  : .:|          |:::  :  | :  : :   |
        48  GVHELLCMVSRA..................CAPKMQTAYGIKAQRSADFS   79

223  RHVFSSGSRELDDLLGGGVRSAVLTELVGESGSGKTQMAIQVCTYAALGL  272
            . :..|  :|:  ||  ::   | ::|: :||||||:  ::..:.|:|
        80  PAFLSTTLSALDEALHGGVACGSLTEITGPPGCGKTQFCIMMSILATL.   127

273  VPLSQADDHDKGNNTFQSRTFVRDPIHASTKDDTLSDILQSYGMEPSIGS  322
                                                 .:.:.
       128  ..................................PTNMGGLEG......  136

323  HRGMGACYITSGGERAAHSIVNRALELASFAINERFDRVYPVCDPTQSSQ  372
            :::  :.:   :| :.  .|:.|  |
       137  .....AVVYIDTESAFSAERLVEIA................ESRFPRYF.  164

373  DADGRRDALLAKAQQLGRRQALANLHIACVADVEALEHALKYSLPGLIRR  422
                 ||  ::  :.: :..|:.:.|.|:|.||    |:.:|.
       165  ...NTEEKLLTSSKVHLYRELTCDEV..LQRIESLEEEI..........  199
```

FIG.2C

```
423 LWSSKRQSGVSREIGVVVVVDNLPALFQQDQAAASDIDSLFQRSKMLVEIA 472
     :|::|   |::|:::.|..|.|  :.|:  .|.:| .|.|.|.
200 ...........ISKGIKLVILDSVASVVRKEFDAQLQ.GNLKERNKFLAREA 239

473 DALKRISAVQWRGASDCGSSAGRAVLVLNHVSDAFGIDKQIARRFVFDSA 522
                                  .:.:.|.:.|..:|.|.:..::
240 ..SSLK....................YLAEEFSIPVILTNQITTHL..... 263

573 SGLLASIAPTLAEAVGARELDSACASNDVPLRTLEARTAQLGQTWSNLIN 622
    ||.|||.:|| ||  .: :..  :::|.|.|                |
264 SGALASQADLVSPADDLSLSEGTSGSSCV..............IAALGNTWSHSVN 305

623 VRVFL.....SKTRARICMRDDQAPACEPVRQNTNQRGTASKSLMNTVRKA 668
     .:|:|            ||                          |: |::
306 TRLILQYLDSERRQILIAKSPLLAP....................FTSFVYTIKEE 340

669 AVVINPFGAT 678
    ::.|.:|::..
341 GLVLQAYGNS 350
```

FIG. 2D

SEQUENCE LISTING

<160> NUMBER OF SEQ ID NOS: 8

<210> SEQ ID NO 1
<211> LENGTH: 350
<212> TYPE: PRT
<213> ORGANISM: Homo Sapiens

<400> SEQUENCE: 1

```
Met Gly Ser Lys Lys Leu Lys Arg Val Gly Leu Ser Gln Glu Leu Cys
 1               5                  10                  15

Asp Arg Leu Ser Arg His Gln Ile Leu Thr Cys Gln Asp Phe Leu Cys
             20                  25                  30

Leu Ser Pro Leu Glu Leu Met Lys Val Thr Gly Leu Ser Tyr Arg Gly
         35                  40                  45

Val His Glu Leu Leu Cys Met Val Ser Arg Ala Cys Ala Pro Lys Met
     50                  55                  60

Gln Thr Ala Tyr Gly Ile Lys Ala Gln Arg Ser Ala Asp Phe Ser Pro
65                  70                  75                  80

Ala Phe Leu Ser Thr Thr Leu Ser Ala Leu Asp Glu Ala Leu His Gly
                 85                  90                  95

Gly Val Ala Cys Gly Ser Leu Thr Glu Ile Thr Gly Pro Pro Gly Cys
            100                 105                 110

Gly Lys Thr Gln Phe Cys Ile Met Met Ser Ile Leu Ala Thr Leu Pro
        115                 120                 125

Thr Asn Met Gly Gly Leu Glu Gly Ala Val Val Tyr Ile Asp Thr Glu
    130                 135                 140

Ser Ala Phe Ser Ala Glu Arg Leu Val Glu Ile Ala Glu Ser Arg Phe
145                 150                 155                 160

Pro Arg Tyr Phe Asn Thr Glu Glu Lys Leu Leu Leu Thr Ser Ser Lys
                165                 170                 175

Val His Leu Tyr Arg Glu Leu Thr Cys Asp Glu Val Leu Gln Arg Ile
            180                 185                 190

Glu Ser Leu Glu Glu Glu Ile Ile Ser Lys Gly Ile Lys Leu Val Ile
        195                 200                 205

Leu Asp Ser Val Ala Ser Val Val Arg Lys Glu Phe Asp Ala Gln Leu
    210                 215                 220

Gln Gly Asn Leu Lys Glu Arg Asn Lys Phe Leu Ala Arg Glu Ala Ser
225                 230                 235                 240

Ser Leu Lys Tyr Leu Ala Glu Glu Phe Ser Ile Pro Val Ile Leu Thr
                245                 250                 255

Asn Gln Ile Thr Thr His Leu Ser Gly Ala Leu Ala Ser Gln Ala Asp
            260                 265                 270

Leu Val Ser Pro Ala Asp Asp Leu Ser Leu Ser Glu Gly Thr Ser Gly
        275                 280                 285

Ser Ser Cys Val Ile Ala Ala Leu Gly Asn Thr Trp Ser His Ser Val
    290                 295                 300

Asn Thr Arg Leu Ile Leu Gln Tyr Leu Asp Ser Glu Arg Arg Gln Ile
305                 310                 315                 320

Leu Ile Ala Lys Ser Pro Leu Ala Pro Phe Thr Ser Phe Val Tyr Thr
                325                 330                 335

Ile Lys Glu Glu Gly Leu Val Leu Gln Ala Tyr Gly Asn Ser
            340                 345                 350
```

-continued

```
<210> SEQ ID NO 2
<211> LENGTH: 1797
<212> TYPE: DNA
<213> ORGANISM: Homo Sapiens

<400> SEQUENCE: 2
cggacgcgtg ggcgcgggga aactgtgtaa agggtgggga aacttgaaag ttggatgctg      60
cagacccggc atgggtagca agaaactaaa acgagtgggt ttatcacaag agctgtgtga     120
ccgtctgagt agacatcaga tccttacctg tcaggacttt ttatgtcttt ccccactgga     180
gcttatgaag gtgactggtc tgagttatcg aggtgtccat gaacttctat gtatggtcag     240
cagggcctgt gccccaaaga tgcaaacggc ttatgggata aaagcacaaa ggtctgctga     300
tttctcacca gcattcttat ctactaccct ttctgctttg gacgaagccc tgcatggtgg     360
tgtggcttgt ggatccctca cagagattac aggtccacca ggttgtggaa aaactcagtt     420
ttgtataatg atgagcattt tggctacatt acccaccaac atgggaggat agaaggagc      480 tgtggtgtac attgacacag agtctgcatt tagtgctgaa agactggttg aaatagcaga     540
atcccgtttt cccagatatt ttaacactga agaaaagtta cttttgacaa gtagtaaagt     600
tcatctttat cgggaactca cctgtgatga agttctacaa aggattgaat ctttggaaga     660
agaaattatc tcaaaaggaa ttaaacttgt gattcttgac tctgttgctt ctgtggtcag     720
aaaggagttt gatgcacaac ttcaaggcaa tctcaaagaa agaaacaagt tcttggcaag     780
agaggcatcc tccttgaagt atttggctga ggagttttca atcccagtta tcttgacgaa     840
tcagattaca acccatctga gtggagccct ggcttctcag gcagacctgg tgtctccagc     900
tgatgatttg tccctgtctg aaggcacttc tggatccagc tgtgtgatag ccgcactagg     960
aaatacctgg agtcacagtg tgaataccccg gctgatcctc cagtaccttg attcagagag    1020
aagacagatt cttattgcca gtccccctct ggctcccttc acctcatttg tctacaccat    1080
caaggaggaa ggcctggttc ttcaagccta tggaaattcc tagagacaga taaatgtgca    1140
aacctgttca tcttgccaag aaaaatccgc ttttctgcca cagaaacaaa atattgggaa    1200
agagtcttgt ggtgaaacac ccatcgttct ctgctaaaac atttggttgc tactgtgtag    1260
actcagctta agtcatggaa ttctagagga tgtatctcac aagtaggatc aagaacaagc    1320
ccaacagtaa tctgcatcat aagctgattt gataccatgg cactgacaat gggcactgat    1380
ttgataccat ggcactgaca atgggcacac agggaacagg aaatgggaat gagagcaagg    1440
gttgggttgt gttcgtggaa cacataggtt tttttttta actttctctt tctaaaatat     1500
ttcattttga tggaggtgaa atttatataa gatgaaatta accatttaa agtaaacaat     1560 tccgtggcaa ctagatatca tgatgtgcaa ccagcatctc tgtctagttc ccaaatattt    1620
catcaccccc aaaagcaaga cccataacca ttatgcaagt gttcctattt cccctcctc     1680 ccagctcctg ggaaaccacc aatctacttt ttttctatgg ctttacctaa tctggaaatt    1740
tcaaataaat gggatcaaat agtttcccaa aaaaaaaaa aaaaaaaaa aaaaaaa        1797

<210> SEQ ID NO 3
<211> LENGTH: 350
<212> TYPE: PRT
<213> ORGANISM: Mus Musculus

<400> SEQUENCE: 3

Met Ser Ser Lys Lys Leu Arg Arg Val Gly Leu Ser Pro Glu Leu Cys
  1               5                  10                  15

Asp Arg Leu Ser Arg Tyr Leu Ile Val Asn Cys Gln His Phe Leu Ser
```

```
                    20                  25                  30
Leu Ser Pro Leu Glu Leu Met Lys Val Thr Gly Leu Ser Tyr Arg Gly
            35                  40                  45

Val His Glu Leu Leu His Thr Val Ser Lys Ala Cys Ala Pro Gln Met
 50                  55                  60

Gln Thr Ala Tyr Glu Leu Lys Thr Arg Arg Ser Ala His Leu Ser Pro
65                  70                  75                  80

Ala Phe Leu Ser Thr Thr Leu Cys Ala Leu Asp Glu Ala Leu His Gly
                85                  90                  95

Gly Val Pro Cys Gly Ser Leu Thr Glu Ile Thr Gly Pro Pro Gly Cys
            100                 105                 110

Gly Lys Thr Gln Phe Cys Ile Met Met Ser Val Leu Ala Thr Leu Pro
            115                 120                 125

Thr Ser Leu Gly Gly Leu Glu Gly Ala Val Val Tyr Ile Asp Thr Glu
        130                 135                 140

Ser Ala Phe Thr Ala Glu Arg Leu Val Glu Ile Ala Glu Ser Arg Phe
145                 150                 155                 160

Pro Gln Tyr Phe Asn Thr Glu Glu Lys Leu Leu Leu Thr Ser Ser Arg
                165                 170                 175

Val His Leu Cys Arg Glu Leu Thr Cys Glu Gly Leu Leu Gln Arg Leu
            180                 185                 190

Glu Ser Leu Glu Glu Glu Ile Ile Ser Lys Gly Val Lys Leu Val Ile
            195                 200                 205

Val Asp Ser Ile Ala Ser Val Val Arg Lys Glu Phe Asp Pro Lys Leu
        210                 215                 220

Gln Gly Asn Ile Lys Glu Arg Asn Lys Phe Leu Gly Lys Gly Ala Ser
225                 230                 235                 240

Leu Leu Lys Tyr Leu Ala Gly Glu Phe Ser Ile Pro Val Ile Leu Thr
                245                 250                 255

Asn Gln Ile Thr Thr His Leu Ser Gly Ala Leu Pro Ser Gln Ala Asp
            260                 265                 270

Leu Val Ser Pro Ala Asp Asp Leu Ser Leu Ser Glu Gly Thr Ser Gly
            275                 280                 285

Ser Ser Cys Leu Val Ala Ala Leu Gly Asn Thr Trp Gly His Cys Val
290                 295                 300

Asn Thr Arg Leu Ile Leu Gln Tyr Leu Asp Ser Glu Arg Arg Gln Ile
305                 310                 315                 320

Leu Ile Ala Lys Ser Pro Leu Ala Ala Phe Thr Ser Phe Val Tyr Thr
                325                 330                 335

Ile Lys Gly Glu Gly Leu Val Leu Gln Gly His Glu Arg Pro
            340                 345                 350

<210> SEQ ID NO 4
<211> LENGTH: 1525
<212> TYPE: DNA
<213> ORGANISM: Mus Musculus

<400> SEQUENCE: 4
gggagccctg gaaacatgag cagcaagaaa ctaagacgag tgggtttatc tccagagctg      60
tgtgaccgtt taagcagata cctgattgtt aactgtcagc acttttttaag tctctcccca    120 ctagaactta tgaaagtgac tggcctgagt tacagaggtg tccacgagct tcttcataca    180
gtaagcaagg cctgtgcccc gcagatgcaa acggcttatg agttaaagac acgaaggtct    240
gcacatctct caccggcatt cctgtctact accctgtgcg ccttggatga agcattgcac    300
```

-continued

```
ggtggtgtgc cttgtggatc tctcacagag attacaggtc caccaggttg cggaaaaact    360
cagttttgca taatgatgag tgtcttagct acattaccta ccagcctggg aggattagaa    420
ggggctgtgg tctacatcga cacagagtct gcatttactg ctgagagact ggttgagatt    480
gcggaatctc gttttccaca atattttaac actgaggaaa aattgcttct gaccagcagt    540
agagttcatc tttgccgaga gctcacctgt gaggggcttc tacaaaggct tgagtctttg    600
gaggaagaga tcatttcgaa aggagttaag cttgtgattg ttgactccat tgcttctgtg    660
gtcagaaagg agtttgaccc gaagcttcaa ggcaacatca agaaaggaa caagttcttg    720 ggcaaaggag cgtccttact gaagtacctg gcagggagt tttcaatccc agttatcttg    780
acgaatcaaa ttacgaccca tctgagtgga gccctccctt ctcaagcaga cctggtgtct    840
ccagctgatg atttgtccct gtctgaaggc acttctggat ccagctgttt ggtagctgca    900
ctaggaaaca catggggtca ctgtgtgaac acccggctga ttctccagta ccttgattca    960
gagagaaggc agattctcat tgccaagtct cctctggctg ccttcacctc ctttgtctac   1020
accatcaagg gggaaggcct ggttcttcaa ggccacgaaa gaccataggg atactgtgac   1080 cttttgtctag tgctgattgc atgtgactca tgaaatgaaa caggactgcg ctgcttggaa   1140
aaaggaaacg gaagccaaca taatgaggat taattggttg gttgctgttg aggtggtaac   1200
agtgatttca gacccggaag gtgaagatga agaagccttt atccagtctc tggatgcaga   1260
ggctaggggc tccaccaccg tgggatgtca gcggccatcg taataatttg cacttacaca   1320
agcacctttc agccatgccc ctcaaagtgg ttcagccaca ttaattaatt aaagcccaca   1380 atcccctag ggagagcagg aggggactac acaagatttg taattacaga agggaaaatt   1440
tccgaataaa gtattgttcc gccaaaaaaa aaaaaaaaaa aaaaaaaaaa aaaaaaaaa   1500 aaaaaaaaaa aaaaaaaaaa aaaaa                                        1525
```

<210> SEQ ID NO 5
<211> LENGTH: 7
<212> TYPE: PRT
<213> ORGANISM: Artificial Sequence
<220> FEATURE:
<223> OTHER INFORMATION: Substrate of ser/thr kinases

<400> SEQUENCE: 5

Leu Arg Arg Ala Ser Leu Gly
 1               5

<210> SEQ ID NO 6
<211> LENGTH: 32
<212> TYPE: DNA
<213> ORGANISM: Artificial Sequence
<220> FEATURE:
<223> OTHER INFORMATION: PCR Primer

<400> SEQUENCE: 6
gagctcgagg gtacccatgg gtagcaagaa ac                                  32

<210> SEQ ID NO 7
<211> LENGTH: 13
<212> TYPE: PRT
<213> ORGANISM: Artificial Sequence
<220> FEATURE:
<223> OTHER INFORMATION: Fragment of Naturally Occurring Protein

<400> SEQUENCE: 7

Arg Arg Leu Ile Glu Asp Ala Glu Tyr Ala Ala Arg Gly

```
                           -continued
1              5              10

<210> SEQ ID NO 8
<211> LENGTH: 20
<212> TYPE: PRT
<213> ORGANISM: Artificial Sequence
<220> FEATURE:
<223> OTHER INFORMATION: Fragment of Naturally Occurring Protein

<400> SEQUENCE: 8

Val Glu Ile Ala Glu Ser Arg Phe Pro Arg Tyr Phe Asn Thr Glu Glu
 1               5                  10                  15

Lys Leu Leu Leu
            20
```

REC 2 KINASE

This is a divisional of application(s) Ser. No. 09/157,603 filed on Sep. 21, 1998 and which designated the U.S. which is incorporated herein by reference in its entirety.

1. FIELD OF THE INVENTION

The present invention concerns the field of molecular genetics and medicine. Particularly, it concerns a gene encoding a protein that is a kinase and is involved in cell cycle regulation and the repair of damaged genomic DNA in mammalian cells. The gene and protein, termed herein, respectively hsREC2 and hsRec2, is in the same supergene family as the mammalian protein having homologous pairing and strand transfer activities, RAD51 and was isolated because of its homology to the homologous pairing and strand transfer protein of *U. stilago maydis*. Due to this relationship the same gene and protein is termed elsewhere RAD51B and Rad51B.

2. BACKGROUND OF THE INVENTION

2.1 The Structure and Function of hsREC2

During the life of every organism the DNA of its cells is constantly subjected to chemical and physical events that cause alterations in its structure, i.e., potential mutations. These potential mutations are recognized by DNA repair enzymes found in the cell because of the mismatch between the strands of the DNA. To prevent the deleterious effects that would occur if these potential mutations became fixed, all organisms have a variety of mechanisms to repair DNA mismatches. In addition, higher animals have evolved mechanisms whereby cells having highly damaged DNA, undergo a process of programmed death ("apoptosis").

The association between defects in the DNA mismatch repair and apoptosis inducing pathways and the development, progression and response to treatment of oncologic disease is widely recognized, if incompletely understood, by medical scientists. Chung, D. C. & Rustgi, A. K., 1995, Gastroenterology 109:1685–99; Lowe, S. W., et al., 1994, Science 266:807–10. Therefore, there is a continuing need to identify and clone the genes that encode proteins involved in DNA repair and DNA mismatch monitoring.

Studies with bacteria, fungi and yeast have identified three genetically defined groups of genes involved in mismatch repair processes. The groups are termed, respectively, the excision repair group, the error prone repair group and the recombination repair group. Mutants in a gene of each group result in a characteristic phenotype. Mutants in the recombination repair group in yeast result in a phenotype having extreme sensitivity to ionizing radiation, a sporulation deficiency, and decreased or absent mitotic recombination. Petes, T. D., et al., 1991, in Broach, J. R., et al., eds., THE MOLECULAR BIOLOGY OF THE YEAST SACCHAROMYCES, pp. 407–522 (Cold Spring Harbor Press, 1991).

Several phylogenetically related genes have been identified in the recombination repair group: recA, in *E. Coli*, Radding, C. M., 1989, Biochim. Biophys. Acta 1008:131–145; RAD51 in *S. cerevisiae*, Shinohara, A., 1992, Cell 69:457–470, Aboussekhra, A. R., et al., 1992, Mol. Cell. Biol. 12:3224–3234, Basile, G., et al., 1992, Mol. Cell. Biol. 12:3235–3246; RAD57 in *S. cerevisiae*, Gene 105:139–140; REC2 in *U. maydis*, Bauchwitz, R., & Holloman, W. K., 1990, Gene 96:285–288, Rubin, B. P., et al., 1994, Mol. Cell. Biol. 14:6287–6296. A third *S. cerevisiae* gene DMC1, is related to recA, although mutants of DMC1 show defects in cell-cycle progression, recombination and meiosis, but not in recombination repair.

The phenotype of REC2 defective *U. maydis* mutants is characterized by extreme sensitivity to ionizing radiation, defective mitotic recombination and interplasmid recombination, and an inability to complete meiosis. Holliday, R., 1967, Mutational Research 4:275–288. UmREC2, the REC2 gene product of *U. maydis*, has been extensively studied. It is a 781 amino acid ATPase that, in the presence of ATP, catalyzes the pairing of homologous DNA strands in a wide variety of circumstances, e.g., UmREC2 catalyzes the formation of duplex DNA from denatured strands, strand exchange between duplex and single stranded homologous DNA and the formation of a nuclease resistant complex between identical strands. Kmiec, E. B., et al., 1994, Mol. Cell. Biol. 14:7163–7172. UmREC2 is unique in that it is the only eukaryotic ATPase that forms homolog pairs, an activity it shares with the *E. coli* enzyme recA.

U.S. patent application, Ser. No. 08/373,134, filed Jan. 17, 1995, by W. K. Holloman and E. B. Kmiec discloses REC2 from *U. maydis*, methods of producing recombinant UmREC2 and methods of its use. Prior to the date of the present invention a fragment of human REC2 cDNA was available from the IMAGE consortium, Lawrence Livermore National Laboratories, as plasmid p153195. Approximately 400 bp of the sequence of p153195 had been made publicly available on dbEST database.

The scientific publication entitled: ISOLATION OF HUMAN AND MOUSE GENES BASED ON HOMOLOGY TO REC2, July 1997, Proc. Natl. Acad. Sci. 94, 7417–7422 by Michael C. Rice et al., discloses the sequences of murine and human Rec2, of the human REC2 cDNA, and discloses that irradiation increases the level of hsREC2 transcripts in primary human foreskin fibroblasts. The scientific publication Albala et al., December 1997, Genomics 46, 476–479 also discloses the sequence of the same protein and cDNA which it terms RAD51B. A sequence that is identical to hsREC2 except for the C-terminal 14 nucleotides of the coding sequence and the 3'-untranslated sequence was published by Cartwright R., et al., 1998, Nucleic Acids Research 26, 1653–1659 and termed hsR51h2. It is believed that hsREC2 and hsR51h2 represent alternative processing of the same primary transcript. The parent application of this application was published as WO 98/11214 on Mar. 19, 1998.

The structure of hsREC2 is also disclosed in application Ser. No. 60/025,929, filed Sep. 11, 1996, application Ser. No. 08/927,165, filed Sep. 11, 1997, and patent publication WO 98/11214, published Mar. 19, 1998.

2.2 Cell Cycle Regulation

The eukaryotic cell cycle consists of four stages, $G_1$, S (synthesis), $G_2$, and M (mitosis). The underlying biochemical events that determine the stage of the cell and the rate of progression to the next stage is a series of kinases, e.g., cdk2, cdc2, which are regulated and activated by labile proteins that bind them, termed cyclins, e.g., cyclin D, cyclin E, Cyclin A. The activated complex in turn phosphorylates other proteins which activates the enzymes that are appropriate for each given stage of the cycle. Reviewed, Morgan, D. O., 1997, Ann. Rev. Cell. Dev. Biol. 15, 261–291; Clurman, B. E., & Roberts, J. M., 1998, in THE GENETIC BASIS OF HUMAN CANCER, pp.173–191 (ed. by Vogelstein, B., & Kinzer K. W., McGraw Hill, N.Y.) (hereafter Vogelstein)

The cell cycle contains a check point in $G_1$. Under certain conditions, e.g., chromosomal damage or mitogen deprivation, a normal cell will not progress beyond the check point. Rb and p53 are proteins involved in the $G_1$ check point related to mitogen deprivation and chromosomal damage, respectively. Inactivating mutations in either of these proteins results, in concert with other mutations, in a growth transformed, i.e., malignant, cell. The introduction of a copy of the normal p53 or Rb gene suppresses the transformed phenotype. Accordingly genes, such as p53 or Rb, whose absence is associated with transformation are termed "tumor suppressor" genes. A frequent cause of familial neoplastic syndromes is the inheritance of a defective copy of a tumor suppressor gene. Reviewed Fearson, E. R., in Vogelstein pp. 229–236.

The level of p53 increases in response to chromosomal damage, however, the mechanism which mediates this response is unknown. It is known that p53 can be phosphorylated by a variety of kinases and that such phosphorylation may stabilize the p53 protein. Reviewed Agarwal, M. L., et al., Jan. 2, 1998, J. Biol. Chem. 273, 1–4.

3. SUMMARY OF THE INVENTION

The present invention is based on the unexpected discovery that hsRec2 is a serine kinase that phosphorylates several proteins that control the cell cycle, particularly cyclin E and p53. The invention permits the phosphorylation of the cell cycle control proteins at sites that are physiologically elevant. In addition, the discovery of the enzyme activity of Rec2 permits the construction of assays for the discovery of compounds that are specific antagonists and agonists of Rec2, which compounds have a pharmacological activity.

4. BRIEF DESCRIPTION OF THE FIGURES

FIGS. 1A–1G. FIGS. 1A and 1B show the derived amino acid sequence of hsREC2 (SEQ ID NO:1) and FIGS. 1C and 1D show the nucleic acid sequences of the hsREC2 cDNA coding strand (SEQ ID NO:2). FIGS. 1E and 1F show the derived amino acid sequence of muREC2 (SEQ ID NO:3) and FIG. 1G shows the nucleic acid sequences of the muREC2 cDNA coding strand (SEQ ID NO:4).

FIGS. 2A–2D. FIG. 2A is an annotated amino acid sequence of hsREC2. Specifically noted are the nuclear localization sequence ("NLS"), A Box and B Box motif sequences, DNA binding sequence and a src-type phosphorylation site ("P"). FIG. 2B is a cartoon of the annotated sequence, showing in particular that the region 80–200 is most closely related to recA. FIGS. 2C and 2D show the sequence homology between hsREC2 and *Ustilago maydis* REC2. The region of greatest similarity, 43% homology, is in bold.

Figure 3A:
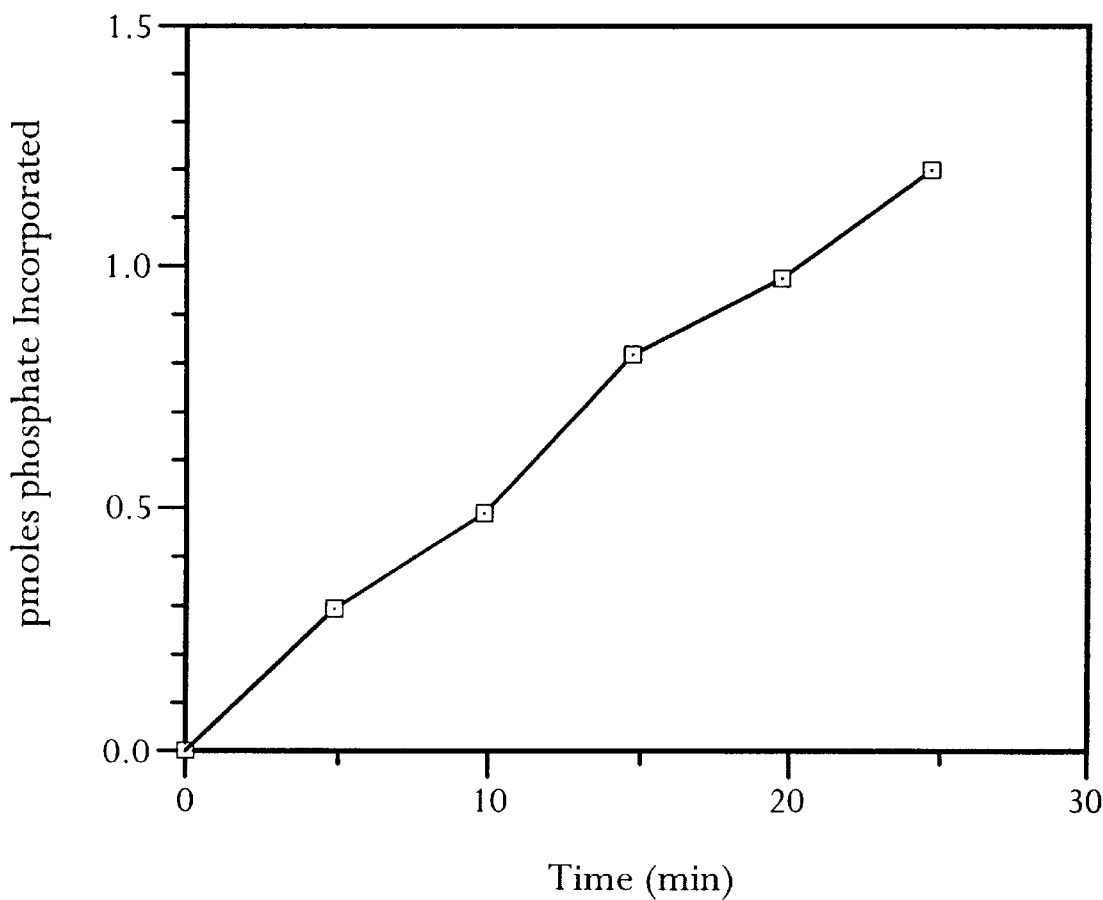
Figure 3B:
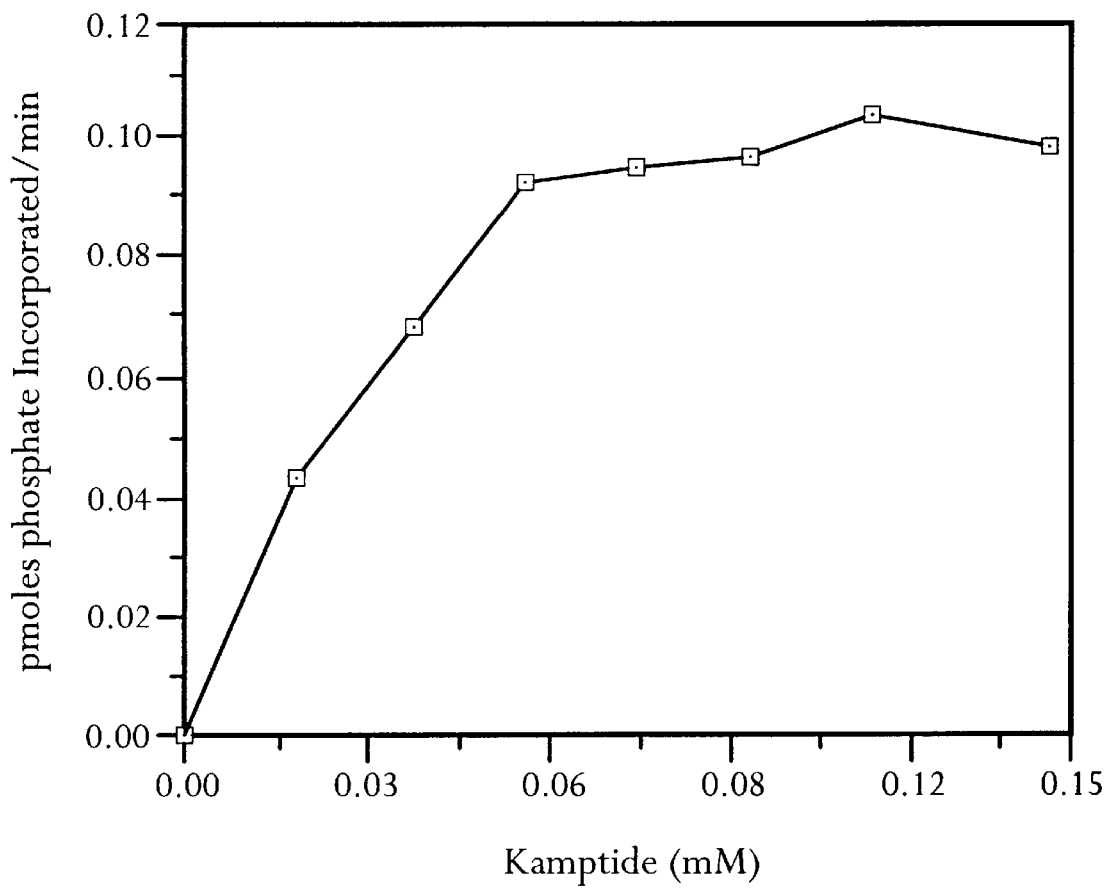

FIG. 3A–3B. A. The incorporation of $^{32}$P-ATP into myelin basic protein (0.25 μM) as a function of time, concentration of Rec2 was 1 μg/30–40 μl. B. The incorporation of $^{32}$P-ATP into kemptide (LRRASLG, SEQ ID No: 5) during a 60 min. reaction as a function of kemptide concentration.

5. DETAILED DESCRIPTION OF THE INVENTION

As used herein, genes are all capitlized, e.g., hsREC2, while the corresponding protein is in initial capitalization, e.g., hsRec2.

The activity of hsREC2 was determined using an N-terminal hexahistadyl containing derivative that was produced in baculovirus. Confirming results were obtained with baculovirus produced glutathione-S-transferase conjugated hsREC2 and with thioredoxin-conjugated hsREC2 produced in *E. coli*. These confirming results tend to exclude that the kinase activity resulted from the co-purification of an endogenous baculovirus kinase on the Ni-NTA resin. To further exclude the possibility of purification artifacts the Ni-NTA purified hexahistadyl-hsREC2 was further purified by preparative SDS-PAGE. Only the fractions containing hsREC2 by silver stain were found to contain kinase activity.

The sequence of muRec2 and hsRec2 differ at only 56 of the 350 amino acids. The invention can be practiced using either muRec2 or hsRec2 or a protein that consists of a mixture of amino acids, i.e., at some positions the amino acid is that of muRec2 and at others the amino acid is that of hsRec2, hereafter a chimeric hs/muRec2. In addition, the mutein having a substitution for the tyrosine at position 163 can be used to practice the invention, e.g., Tyr→Ala. Thus, the invention can be further practiced using a chimeric hs/muREC2$^{ala163}$. In one embodiment the substitution can be any aliphatic amino acid. In an alternative embodiment the substitution can be any amino acid other than cysteine or proline. The term "Rec2 kinase" is used herein to denote the genus consisting of hsRec2, muRec2 and all chimeric hs/muRec2 proteins and the Tyr$^{163}$ substituted derivatives of each. The term artificial Rec2 kinase is a Rec2 kinase that is not also a mammalian Rec2. The term mammalian Rec2 is used herein to denote the genus of proteins consisting of the mammalian homologs of hsRec2 and of muRec2.

The invention can further be practiced using a fusion protein, which consists of a protein having a sequence that comprises that of a Rec2 kinase or a mammalian Rec2 that is fused to a second sequence which is a protein or peptide that can be used to purify the resultant fusion protein.

The naturally occurring hsRec2 and muRec2 are found as phosphoproteins, the phosphorylation of which is not essential to the activity of the proteins as a kinase. In, the invention the terms Rec2 kinase and mammalian Rec2 encompass both the phosphorylated and non-phosphorylated forms of the proteins.

5.1 Cell Cycle Regulation

An expression vector comprising hsREC2 operably linked to the CMV immediate early promoter was constructed and transfected into CHO cells. A mutein was constructed in which tyrosine-163, a phosphorylatable tyrosine in an src site (phe-pro-arg-tyr) (amino acids 8–11 of SEQ ID No. 8) was replaced by alanine (hsREC2$^{ala163}$). Sham (neo$^r$) transfected, hsREC2 transfected and hsREC2$^{ala163}$ transfected CHO cells were synchronized by serum starvation, released, and the DNA content was assayed by quantitative fluorescent flow cytometry at various time points. The hsREC2 transfected cells showed delayed onset of S phase. Thus, at 14 hours post release 75% of the hsREC2 transfected cells were in $G_1$ compared to 36% of the controls.

Over expression of hsREC2 but not hsREC2$^{ala163}$ sensitizes the cell to UV radiation. CHO cells were irradiated with UV at 15 J/m$^2$. Again the cells were analyzed by quantitative fluorescent flow cytometry The hsREC2 cells showed extensive apoptosis compared to the controls at 24, 48 and 72 hours post irradiation.

5.2 Kinase Activity

The kinase activity of hsREC2 can be shown on a variety of substrates. Artifactual substrates such as myelin basic protein, which is a known substrate for protein kinase C and protein kinase A are phosphorylated by hsREC2. The kemptide (leu-arg-arg-ala-ser-leu-gly), which is also a known substrate of ser/thr kinases can be phosphorylated. In addition the following recombinantly produced proteins are phosphorylated by hsREC2: p53, cyclin B1 and cyclin E. The heterodimers of cyclin B1/cdc2 and cyclin E/cdk2 are also phosphorylated by hsREC2. The interpretation of these experiments is complicated by the fact that cyclin E/cdk2 autophosphorylates and that cyclin B1/cdc2 but not cyclin E/cdk2 phosphorylates hsREC2 itself. In contrast to the cyclinB1/cdc2 complex, hsRec2 is not an autophosphorylase.

Although expression of hsREC2$^{ala163}$ in a cell has no effect on the cell cycle, the hsREC2$^{ala163}$ mutein has full kinase activity.

Compounds having pharmacological activity with respect to mREC2 can be identified by assaying the kinase activity of an mREC2, and particularly hsREC2, in the presence of candidate agonists or antagonists. The particular preferred substrates are cyclin E and p53.

5.3 hsREC2 Association With Other Proteins

An S$^{35}$-radiolabeled preparation of hsREC2 was made by coupled transcription translation in a recticulocyte lysate system. The preparation was mixed with an extract from HCT116 cells. In separate reactions monoclonal antibodies to various cell proteins were added and the antibody bound material isolated with Protein A Sepharose. The bound material was then analyzed by SDS-PAGE, and autoradiographed. The immunoprecipitate contained hsREC2 when anti-p53, anti-PCNA and anti-cdc2 monoclonals were used. No hsREC2 was precipitated when anti-cdc4 or anti-cdk4 monoclonals were employed.

5.4 An hsREC2 Agonist or Antagonist Has a Pharmacologic Activity

The activities of hsREC2 indicate that the modulation of its activity can sensitize or desensitize a cell to enter apoptosis as a result of incurring genetic damage, as for example by UV radiation, and can also protect or deprotect a cell from DNA damage by extending or shortening the G$_1$ and S periods. Agonist and antagonists of hsREC2 are compounds having activities of the type that medical practitioners desire. The discovery of compounds that are hsREC2 agonists or antagonists will be important in pharmaceutical science.

In one embodiment, the invention is a method of determining whether a given compound has such a pharmacological activity by measuring the effects of the compound on the kinase activity of hsREC2. In specific embodiments, the invention is a method wherein the relative effects of the compound on hsREC2 and on a second kinase are assessed. For example, a compound that is an agonist of hsREC2, but has little or no effect on cyclin D/cdk4 and cyclin E/cdk2 would cause cells to arrest in G$_1$ and undergo apoptosis in response to genetic damage. In particular embodiments, the kinase assay is done with a substrate that is selected from the group consisting of p53, cdc2, cdk2 or cyclin E. Alternatively, the substrate can be a model substrate such as myelin basic protein or kemptide (leu-arg-arg-ala-ser-leu-gly).

6. EXAMPLES 6.1 The production of recombinant hsREC2 protein by baculovirus infection of *Autographica californica*

To facilitate the construction of an hsREC2 expression vector, restriction sites for XhoI and KpnI were appended by PCR amplification to a the hsREC2 cDNA. The hsREC2 cDNA starting at nt 71 was amplified using the forward primer 5'-GAG CTCGAG GGTACC C ATG GGT AGC AAG AAA C-3' (SEQ ID NO:6), which placed the XhoI and KpnI sites (underlined) 5' of the start codon. The recombinant molecule containing the entire coding sequence of hsREC2 cDNA, can be removed using either XhoI or KpnI and the unique XbaI site located between nt 1270 and 1280 of SEQ ID NO:2.

A vector, pBacGSTSV, for the expression of HsREC2 in baculovirus infected *Spodoptera frugiperda* (Sf-9) insect cells (ATCC cell line No. CRL1711, Rockville Md.), was obtained from Dr. Zailin Yu (Baculovirus Expression Laboratory, Thomas Jefferson University). The vector pVLGS was constructed by the insertion of a fragment encoding a *Schistosoma japonicum* glutathione S-transferase polypeptide and a thrombin cleavage site from pGEX-2T (described in Smith & Johnson, GENE 67:31 (1988)), which is hereby incorporated by reference, into the vector pVL1393. A polyA termination signal sequence was inserted into pVLGS to yield pBacGSTSV. A plasmid containing the 1.2 Kb hsREC2 fragment was cut with KpnI, the 3' unpaired ends removed with T4 polymerase and the product cut with XbaI. The resultant fragment was inserted into a SmaI, XbaI cut pBacGSTSV vector to yield pGST/hsREC2.

Recombinant virus containing the insert from pGST/hsREC2 were isolated in the usual way and Sf-9 cells were infected. Sf-9 cells are grown in SF900II SFM (Gibco/BRL Cat #10902) or TNM-FH (Gibco/BRL Cat #11605-011) plus 10% FBS. After between 3–5 days of culture the infected cells are collected, washed in Ca$^{++}$ and Mg$^{++}$ free PBS and sonicated in 5 ml of PBS plus proteinase inhibitors (ICN Cat #158837), 1% NP-40, 250 mM NaCl per 5×10$^7$ cells. The lysate is cleared by centrifugation at 30,000×g for 20 minutes. The supernatant is then applied to 0.5 ml of glutathione-agarose resin (Sigma Chem. Co. Cat #G4510) per 5×10$^7$ cells. The resin is washed in a buffer of 50 mM Tris-HCl, pH 8.0, 150 mM NaCl and 2.5 mM CaCl$_2$, and the hsREC2 released by treatment with thrombin (Sigma Chem. Co. Cat #T7513) for 2 hours at 23° C. in the same buffer. For certain experiments the thrombin is removed by the technique of Thompson and Davie, 1971, Biochim Biophys Acta 250:210, using an aminocaproyl-p-chlorobenzylmide affinity column (Sigma Chem. Co. Cat #A9527).

Alternatively, the full length hsREC2 cDNA was cloned into the expression vector, pAcHisA, for overexpression in a baculovirus system and purification utilizing a 6 histidine tag. For cloning, the hsREC2 expression cassette was cut with KpnI, the 3' protruding termini were removed with T4 polymerase, and the DNA was then digested with XbaI. The resulting fragment was ligated to pAcHisA using the SmaI and XbaI sites. Recombinant virus containing hsREC2 was purified and insect cells were infected by Dr. Z. Yu in the Baculovirus expression laboratory of the Kimmel Cancer Institute. Insect cell pellets from 2 liters of culture were suspended in 60 ml of 10 mM TrisCl, pH 7.5, 130 mM NaCl, 2% TX100, 2 μg/ml leupeptin and aprotinin and 1 μg/ml pepstatin and sonicated on ice 4 times for 5 seconds each using a microtip at a 20% pulse (Branson sonifier 450). Debris was removed by centrifuging at 30,000×g for 20 minutes. The clarified supernatant was divided between two 50 ml culture tubes and 1 ml of Ni-NTA agarose added to each tube for 1 hour with rocking at 4° C. The unbound fraction was separated from the resin by a brief centrifugation and the resin was washed with 10 ml of 100 mM imidazole for 10 minutes on a rocker and centrifuged at 2000 rpm for 5 minutes. After a second 10 minute wash with 500 mM imidazole the slurry was transferred to a column and the effluent discarded. The purified his-hsRec2 was eluted with 1M imidazole, pH 7.0 (imidazole on column for 10 minutes before collection of eluate), and dialyzed overnight against 50 mM TrisCl, pH 7.4, 50 mM NaCl, 10% glycerol. For simplicity, this protein will be referred to as hsRec2 instead of hishsRec2.

6.2 The Bacterial Production of recombinant hsREC2 protein

The hsREC2 cDNA coding region was excised from the previously used mammalian expression vector pcDNA3 G8 by cleavage with XbaI, removal of 5' protruding termini with T4 polymerase, followed by cleavage with KpnI. The resulting fragment was ligated into the KpnI and blunted HindIII sites of a bacterial expression vector pBAD/HisC (Invitrogen, Corp., USA). The constructed expression vector with hREC2 cloned in frame with a hexahistidine tag was electrotransformed into LMG194 bacteria (Invitrogen, Corp., USA) for expression. A 500 ml LB ampicillin culture was inoculated by a single colony and grown at 37° into log phase. The culture was induced by 0.02% arabinose for 4 hours and harvested by centrifuging at 8,000×g. The pellet was resuspended and lysed by 1 mg/ml lysozyme and sonication in 5 volumes of 50 mM $NaH_2PO_4$, 300 mM NaCl, 1% TX100, 2 µg/ml leupeptin and aprotinin and 1 µg/ml pepstatin, 0.1 mg/ml DNase I, 10 mM βME and 20 mM imidazole at 0° C. The lysate was clarified by centrifugation at 10,000×g for 30 minutes then added to a sealed column containing 1 ml activated Ni+NTA agarose resin and rocked at 4 for 1 hour. The column was then opened and washed by gravity with 20 volumes of 50 mM $NaH_2PO_4$, 300 mM NaCl, 1% TX100, 50 mM imidazole at 4°. The bound protein was then eluted in 3 volumes of the above wash buffer with 500 mM imidazole and collected in 1 ml fractions. The purified His-HsRec2 was dialyzed over night against 50 mM Tris, 50 mM NaCl, 10% glycerol and stored at −80°.

6.3 Detection of hsREC2 Kinase

Phosphokinase filter assays. Substrates were either kemptide or myelin basic protein and approximately 1 µg of his-hsRec2 was added as the phosphokinase. For both assays, the buffer contained 50 mM TrisCl, pH 7.5, 10 mM $MgCl_2$, 1 mM DTT. The second substrate, $^{32}$P-ATP was constant at 50 µM with a specific activity of 1972 cpm/pmole (kemptide) and 2980 cpm/pmole (MBP). $^{32}$P-ATP was added to initiate the reaction which was carried out at 30° C. for the indicated time. At the end of the reaction, 20 µl was spotted on phosphocellulose discs, washed twice with 10 ml per disc in 1% phosphoric acid and twice in distilled water. Filters were counted in a Wallac Scintillation counter. Substrate without hsRec2 added was used as a control and counts were subtracted to obtain a zero point.

Myelin basic protein (0.25 µM) was phosphorylated for between 0 and 25 minutes at the above conditions. Phosphate incorporation was linear with time and reached 1.2 pmole at 25 minutes. Kemptide from 0 to 0.15 mM was phosphorylated for 60 minutes. The rate of phosphate incorporation was linear with substrate concentration up to 0.06 mM, where a rate of 0.09 pmoles/minute was observed.

Two different hsRec2 conjugates, GST-hsRec2 and thioredoxin-hsRec2, also exhibited phosphokinase activity. Further evidence that this activity was not a contaminant, was obtained by immunoprecipitating hsREC2 using hybridoma supernatants, followed by assay for phosphokinase activity using p53 as a substrate as described below. These experiment confirmed that the kinase activity was precipitable by anti-hsREC2 monoclonal antibodies.

Two substrates that were not phosphorylated by hsRec2, were a tyrosine kinase substrate peptide containing one tyrosine, derived from the sequence surrounding the phosphorylation site in pp60$^{src}$ (RRLIEDAEYAARG) (SEQ ID No. 7), and an hsRec2 peptide, residues 153–172 (VEIAESRFPRYFNTEEKLLL) (SEQ ID No. 8).

p53 phosphorylation. Human recombinant p53 (0.5 µg, Pharmingen, San Diego, Calif.) was incubated with or without hsRec2 in 50 mM TrisCl, pH 7.4, 10 mM $MgCl_2$, and 1 mM DTT at 30° C. The reaction was initiated by the addition of $^{32}$P-ATP (25 µM ATP, 40 cpm/femtomole). At the end of each time point an equal volume of 2× loading buffer (5) was added and tubes were placed on ice until all tubes were collected. Samples were then heated at 100° C. for 10 minutes and 13 µl were run on Ready Gels (Bio-Rad Laboratories, Hercules, Calif.), and transferred to nitrocellulose overnight prior to exposure to X-ray film. Radiolabeled p53 was readily observed.

cdc2/cyclin B phosphokinase assay. Purified human recombinant cyclin B1/cdc2 (Oncogene, Cambridge, Mass.), was incubated with hsRec2 for 10 or 60 minutes at 30° C., using the same buffer conditions as described for p53. An equal volume of 2× gel lading buffer was added (5), samples were heated at 100° C. for 10 minutes and run on an SDS gel, transferred to nitrocellulose and exposed to film. Radiolabeled cyclin B1 due to hsREC2 kinase activity was readily observed above the level of "autophosphorylation" of cyclin B1 by cdc2. Radiolabeled cdc2 was observed only in the hsREC2 containing reactions mixtures at 60 minutes but not at 10 minutes reaction time.

cdk2/cyclin E phosphokinase assay. GST-cyclin E was isolated from E. coli transformed with pGEX-2TcycE (A. Giordano, Thomas Jefferson University) and purified using Glutathione Sepharose 4B (Pharmacia, Piscataway, N.J.). The glutathione Sepharose GST-cyclin E was washed, and then stored as a 1:1 slurry in 50 mM Tris Cl, pH 7.4. For assays with cyclin E bound cdk2, purified cdk2 (kindly given to us by A. Koff, Sloan-Kettering, N.Y.) was incubated with cyclin E as described (6) and unbound cdk2 removed by washing prior to storage as a 1:1 slurry. Kinase assays were carried out with the immobilized GST-cyclin E with or without bound cdk2 otherwise using the same conditions described for p53. Phosphorylation of cyclin E and hsREC2 was readily observed in the absence of cdk2. In the presence of cdk2, autophosphorylation was seen, however, hsREC2 phosphorylation of cyclin E above that level was readily apparent.

In vitro associated between p53 and hsRec2. HsRec2 (5 µg) and 15 µl agarose-GST-p53 (Oncogene Sciences) were added to 0.5 ml of binding buffer (10%) glycerol, 50 mM Tris Cl, pH 7.4, 0.1 mM EDTA, 1 mM DTT, 0.02% NP40, 200 mM NaCl, 10 µg/ml aprotinin and leupeptin,and 20 µM PMSF. Following one hour at room temperature, the p53 agarose was pelleted and washed twice with buffer as above, using a higher concentration of detergent (0.1% NP40), and once with 50 mM TrisCl, pH 7.4, 10 mM $MgCl_2$.

Association of in vitro translated hsRec2 with PCNA, p53 and cdc2. XbaI linearized pCMVhREC2 was first transcribed in vitro (Ambion, Austin Tex.) using 1 µg of the vector, and then translated in vitro along with Xef1 mRNA included in the kit as a positive control. Reticulocyte lysates containing Xef1 or hsRec2 translation products labeled with $^{32}$S-methionine were incubated with 1.2 mg cell extract from HCT116 cells (50 mM TrisCl, pH 7.4, 120 mM NaCl, 0.5% NP40, 20 µM PMSF, 2 µg/ml pepstatin, and 10 µg/ml leupeptin and aprotinin, MB) for 2 hours, then 10 µg of antibodies against PCNA, p53 or cdc2 were added for an overnight incubation. On the following day, Protein A Sepharose was added for 2 hours, and pellets were washed four times with 500 µl MB. Pellets were suspended in 40 µl of sample buffer, boiled 10 minutes and 15 µl run on a 10% gel, then transferred to nitrocellulose to obtain a lower background, before exposure to X-ray film.

What is claimed is:

1. A composition comprising:
   a. an enzyme having a sequence that comprises the sequence of a Rec2 kinase;
   b. a serine-containing substrate of the enzyme; and
   c. a γ-phosphate labeled ATP.

2. The composition of claim 1, in which the labeled phosphate comprises a $^{32}P$ atom.

3. The composition of claim 1, in which the substrate is a cell-cycle control protein.

4. The composition of claim 3 in which the substrate is a protein selected from the group consisting of human p53, human cdc2, human cdk2 and human cyclin E.

5. The composition of claim 1, in which the substrate is a kemptide.

6. The composition of claim 1, in which the sequence of the enzyme comprises the sequence of SEQ ID NO:1 or SEQ ID NO:1 having alanine at position 163.

7. An enzyme comprising a Rec2 kinase having an amino acid at position 163 that is other than a tyrosine.

8. An enzyme having at least 84% homology to SEQ ID NO:1 having an amino acid at position 163 that is other than a tyrosine, wherein the enzyme phosphorylates p53 or cyclin E and has a src-like phosphorylation site.

9. A composition comprising:
   a. an enzyme having at least 84% homology to SEQ ID NO:1 wherein said enzyme, phosphorylates p53 or cyclin E and has a src-like phosphorylation site;
   b. a serine-containing substrate of the enzyme; and
   c. a γ-phosphate labeled ATP.

10. The composition of claim 9, in which the labeled phosphate comprises a $^{32}P$ atom.

11. The composition of claim 9, in which the substrate is a cell-cycle control protein.

12. The composition of claim 11, in which the substrate is a protein selected from the group consisting of human p53, human cdc2, human cdk2 and human cyclin E.

13. The composition of claim 9, in which the substrate is a kemptide.

14. The composition of claim 9, in which the sequence of the enzyme comprises the sequence of SEQ ID NO:1 or SEQ ID NO:1 having alanine at position 163.

* * * * *